United States Patent [19]

Scrivo et al.

[11] 4,208,579
[45] Jun. 17, 1980

[54] ELECTRICALLY ISOLATED CONTROL MEANS FOR THE ILLUMINATING SOURCE OF A DENTAL DRILL

[75] Inventors: Leonard Scrivo, Tuckahoe, N.Y.; Paul Binner, Dumont, N.J.; Louis Weinstein, Yardley, Pa.

[73] Assignee: Vicon Products Corp., Pelham Manor, N.Y.

[21] Appl. No.: 972,272

[22] Filed: Dec. 22, 1978

Related U.S. Application Data

[63] Continuation-in-part of Ser. No. 874,911, Feb. 2, 1978, abandoned.

[51] Int. Cl.² .............................................. G02B 27/00
[52] U.S. Cl. .................................... 250/227; 250/551; 250/229; 36/27
[58] Field of Search ....................... 250/551, 229, 227; 360/365 P; 36/27, DIG. 7

[56] References Cited

U.S. PATENT DOCUMENTS

| | | | |
|---|---|---|---|
| 3,999,074 | 12/1976 | Callaghan | 250/551 |
| 4,013,342 | 3/1977 | Narodny | 250/229 X |

Primary Examiner—David C. Nelms
Assistant Examiner—Darwin R. Hostetter
Attorney, Agent, or Firm—Lerner, David, Littenberg & Samuel

[57] ABSTRACT

Apparatus for use in operating a dental drill is disclosed in which the air, water and light for the hand-held drill member are each delivered from an associated supply source, all of which are adapted to be located at a position remote from the working end of the drill and are coupled to the drill through a conduit cable, and in which control means for the selective energization of the light supply source is located within easy reach of the operator to permit turn-on and/or turn-off of the light supply source through simple fingertip control provided within a remote control unit which is totally electrically isolated from the high voltage present in the light supply source to protect both the operator and the patient from shock or injury. The light supply source may be automatically energized merely by lifting the instrument containing the dental fiber optics.

The light unit may be independent of the dental drill to permit a wide variety of uses independently of its use with the dental drill.

44 Claims, 23 Drawing Figures

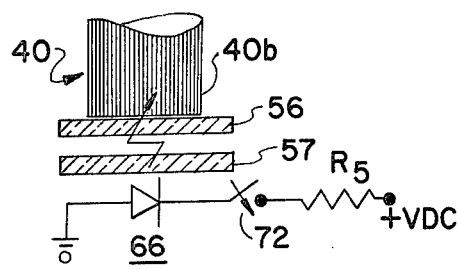
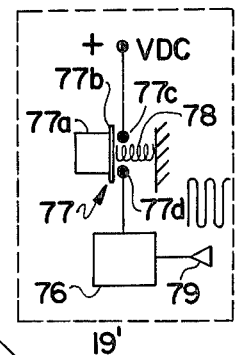
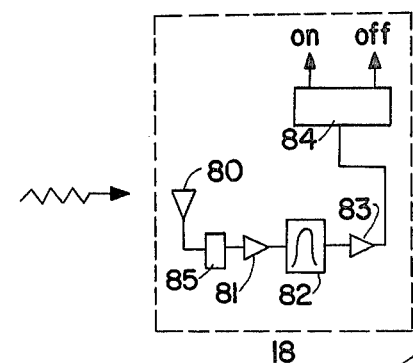
FIG.3e
FIG.3f
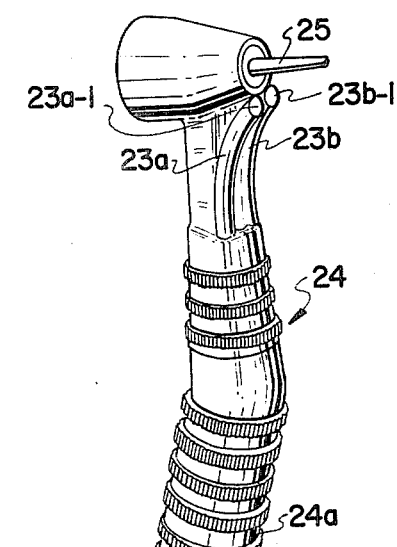
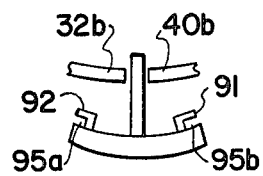
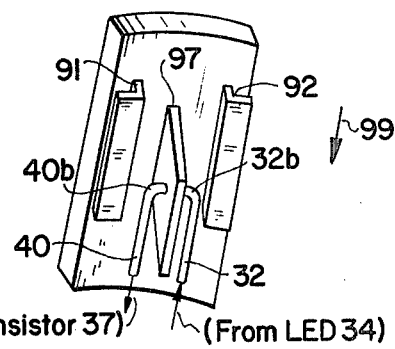
FIG.4
FIG.4a
FIG.4b
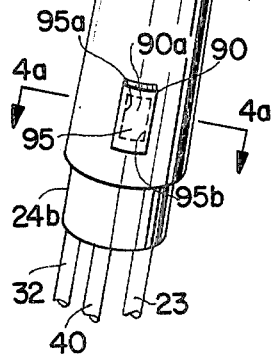
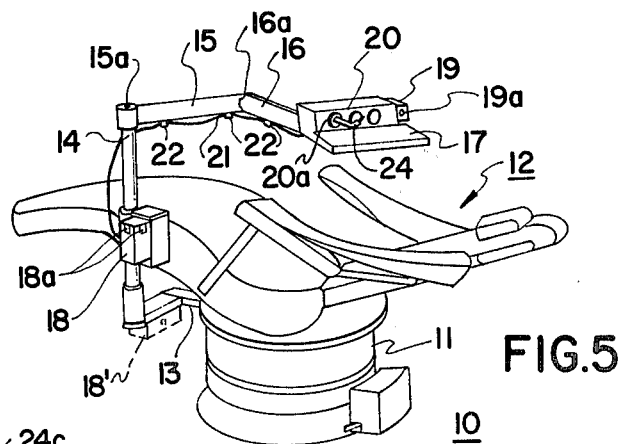
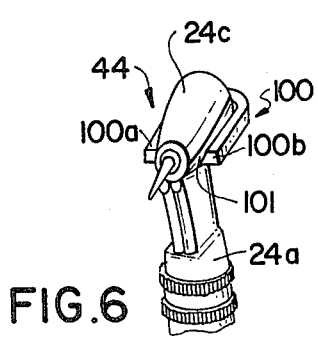
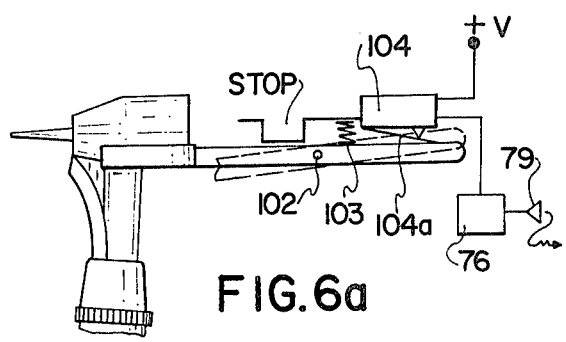
FIG.5
FIG.6
FIG.6a

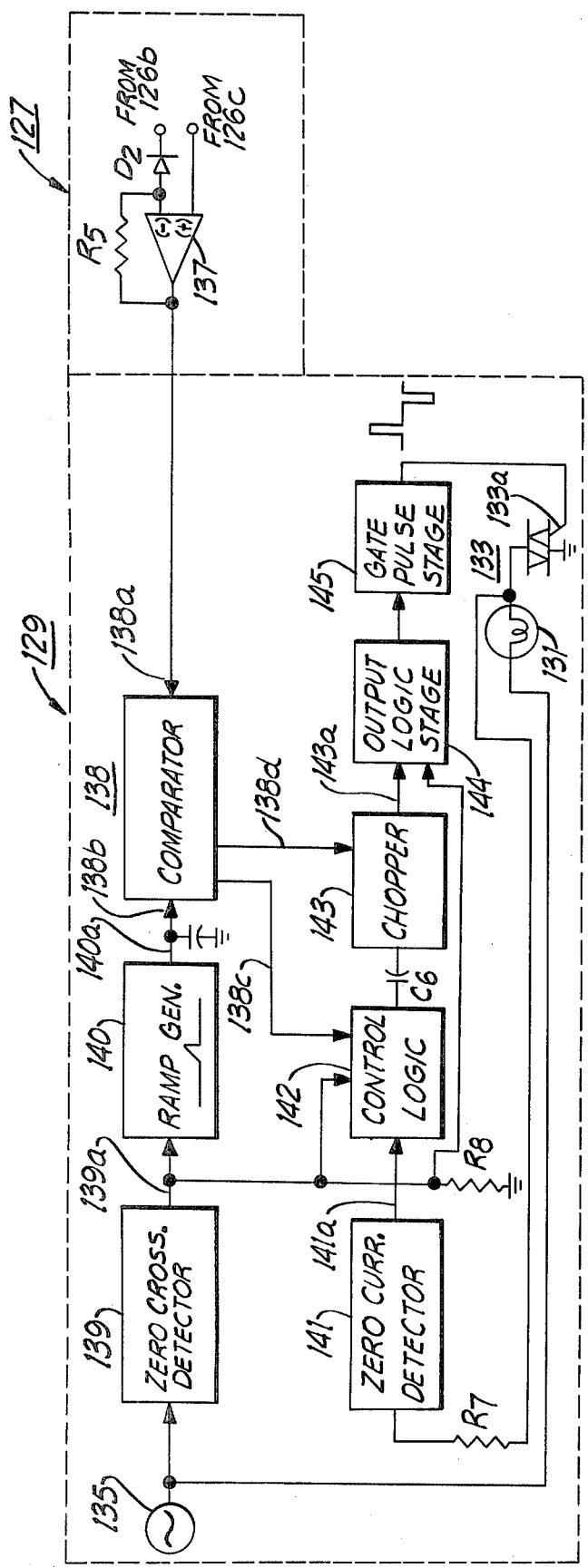
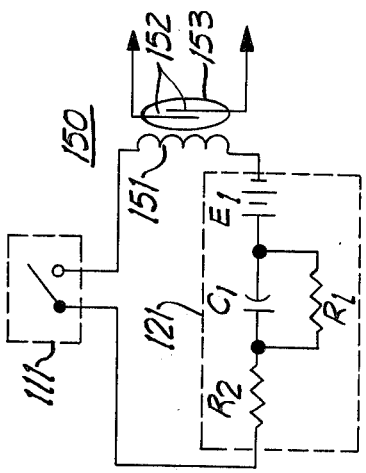
FIG. 7a
FIG. 7b

ELECTRICALLY ISOLATED CONTROL MEANS FOR THE ILLUMINATING SOURCE OF A DENTAL DRILL

This application is a continuation-in-part of application Ser. No. 874,911, filed Feb. 2, 1978, now abandoned.

BACKGROUND OF THE INVENTION

One of the most widely used and important tools employed by dentists and dental hygienists is the hand-held drill which is typically a hand-held piece specifically designed and having a shape which provides for proper orientation within the mouth of the patient without requiring any awkward or unusual contortions on the part of the operator in order to appropriately position the operating end of the hand-held drill piece for the purpose of drilling, cutting, polishing, buffing, hammering, tamping and the like. The patient's mouth is a confined area requiring the skilled operator to exercise a high degree of care in the performance of dental procedures. It is quite imperative that the immediate region of concern be adequately lighted so that the operator is confident that he is performing the proper function in the proper location. This capability has been very adequately provided for in the form of an elongated fiber optic bundle having its proximal end positioned immediately adjacent a source of illumination and having its distal end mounted within the body of the drill handpiece and positioned adjacent the output shaft of the drill to flood the area of concern with light of an adequate level to permit the operator to perform the desired procedures in an assured manner.

The articulated design of the handpiece, tool and supply tray and even the dental chair enable these members to be easily manipulated and movable with the objectives of both patient comfort and operator efficiency in mind. As a result, it is most advantageous and in many cases even necessary to place the lamp source and power unit provided therefore in some location where it does not interfere with the articulated equipment employed by the operator during the performance of normal dental procedures. Since the drill handpiece is normally utilized in an intermittent fashion, it is most efficient and economical to be able to turn the lamp source on and off in a simple and straightforward fashion. This basic capability is adequately provided for as taught by U.S. Pat. No. 3,758,951 issued Sept. 18, 1973, and assigned to the assignee of the present invention, wherein a small, compact, lightweight unit identified therein as a remote control unit (RCU) is adapted to be positioned in the immediate vicinity of the work area, and which is provided with an on/off switch within easy reach of the operator to enable quick and simple turn off or turn on of the lamp source, and wherein the small size of the remote control unit enables the unit to be positioned within easy reach of the operator (typically beneath the articulated tray) without in any way interfering with other apparatus in the vicinity or with the access of the operator to such apparatus.

The conventional approach for such on/off control means is to provide an electrical circuit including switch means mounted within the remote control unit and coupled across a pair of conductive leads extending between the remote control unit and the illuminating lamp supply source. The switch may be selectively turned on and off in order to respectively energize and deenergize the light source to convey light to the area of concern by way of the fiber optics bundles.

Since water is continuously utilized during many of the dental procedures such as, for example, to cool the drill bit and tooth during drilling as well as to periodically rinse a drilled tooth to facilitate examination to determine the progress of any procedure, it is not only important but frequently required by both local and Federal regulations that the level of electrical energy of any electronic components present in the immediate working area be no greater than 21 volts at virtually zero current to protect both operator and patient from electrical shock or injury. With the apparatus of the above-mentioned issued patent, this is accomplished by providing a step-down transformer within the housing of the supply source to reduce the voltage output derived from a conventional wall receptacle typically rated at 115 volts AC, down to the above-mentioned voltage/current level. Although this technique reduces the output power delivered to the remote control unit, the danger of minor shock is still present. In addition thereto, the weight of the step-down transformer required for the above application, together with its size makes the supply source unit unduly large and heavy, serving to increase the cost of the equipment and imposing physical restrictions on both the ease of mounting and the locations in, on or upon which the unit may be mounted.

BRIEF DESCRIPTION OF THE INVENTION

The present invention is characterized by comprising a combination remote control unit and lamp supply source of reduced size and weight as compared with the conventional device described hereinabove, through the use of novel wireless signaling means which simply and yet effectively provides for selective automatic turn on and turn off of the lamp source while totally eliminating the need for an electrical connection between the main supply unit and the remote control unit.

In one preferred embodiment, the compact remote control unit is enclosed within a small housing having bracket means suitable for securing the housing at an easily accessible position on or adjacent to the patient's chair, and typically beneath the tray provided for supporting tools and materials normally used during dental procedures. The larger light source and power supply unit may be mounted at a location remote therefrom so as not to interfere with activities undertaken around the chair by the skilled operator.

The remote control switch means includes a manually operable element which may either be a push button slide member or control knob for activating a miniature signaing device such as a transmitter which may be of either the radio frequency or sonic frequency generator type for generating a carrier frequency signal which is picked up by a small receiver within the main light source and power supply unit to activate a pick up circuit which turns on the main power supply and maintains it in the "on" condition. Subsequent activation of the transmitter in the remote control unit, which is operated on only a momentary basis, turns off the light source and power supply unit when it is no longer needed. This arrangement totally isolates the remote control unit from the power supply so as to completely remove any possibility of injury, or even mild shock to either the patient or the operator, there being a need for only a small battery of the size no larger than that which is typically utilized to power a small pocket flashlight.

This arrangement also totally eliminates the need for the expensive, large size and heavy transformer normally required in the conventional apparatus as depicted in the above-mentioned U.S. Pat. No. 3,758,951.

As another alternative embodiment, a fiber optics bundle is extended between the remote control unit and the light source and power supply unit such that the proximal end is positioned adjacent to a phototransistor while the distal end, contained within the remote control unit, is positioned adjacent to a low power drain light source, preferably a light emitting diode (LED). A miniature battery is utilized as the power source. Switch means serves to provide an electrical connection between the power source and the LED which directs light into the fiber optics bundle to activate the phototransistor, thereby serving to turn on the main power supply.

As a further alternative embodiment, a pair of fiber optics bundles, serving respectively as a "go" and "return" light conduits may be provided with both the LED and phototransistor mounted within the main power supply housing. The proximal ends of the "go" and "return" fiber optics bundles are positioned adjacent to the LED and phototransistor respectively whereas their distal ends are positioned in close proximity to one another. A manually operable switch movable between an open and a closed position serves respectively to couple and decouple (i.e., "block") light from the "go" bundle to the "return" bundle in order to selectively turn on and turn off the power supply again totally eliminating any electrical connection between the remote control unit and the power supply.

The sensing unit may be operated by ambient light wherein a single fiber optics bundle extends between a phototransistor in the supply unit and an opening in the remote control unit, which opening is selectively closed or opened by a slide switch to deactivate or activate the phototransistor with ambient light conveyed to the phototransistor through the fiber optics bundle.

The intensity of the light reaching the phototransistor may be modulated either electrically in one embodiment by an adjustable resistor coupled between the battery and the LED or in another embodiment by attenuating the light passing between the "go" and "return" fiber optics bundles by relative rotation of a pair of polarized lenses.

The switch for controlling the main light source may be mounted upon the dental handpiece, either an an integral part thereof, or secured to the handpiece by a securement strap or other member. This embodiment completely eliminates the remote control unit and combines the additional fiber optic bundles with those already required for conveying the light from the main light source to the distal end of the handpiece. As a further advantageous feature, the lifting of the handpiece from its cradle may be used to automatically activate the main light source.

As still another preferred embodiment of the present invention, control of the source of illumination for the dental handpiece may be accomplished by means of a low voltage battery operated circuit including a switch preferably mounted within the dental handpiece. The normally-open switch is connected in a circuit loop with the battery, a pulse circuit and the light emitting element of an optically coupled isolator which includes a cooperating phototransistor.

The pulse circuit develops a pulse signal responsive to switch closure, which signal is sufficient to cause illumination of the light emitting element. This light output is picked up by the phototransistor to develop a control signal utilized to selectively energize the illumination source for the fiber optics bundle. In an alternative arrangement of the last mentioned embodiment, a logic control circuit including counter means may be provided to accept signals from the optically coupled isolator to provide a brightness level control as well as on/off control for the lamp. A cooling fan which serves to prevent overheating of the illumination source for the fiber optics bundle may also be selectively energized through a similar logic control circuit.

In a simplified version of the above the last mentioned preferred embodiment, through the use of bistable flip-flop in place of the aforesaid counter means, it is possible to alter the control apparatus to simply an on/off control means. As another alternative embodiment, a sonically coupled isolator may be employed in place of the optically coupled isolator, the sonically coupled isolator being comprised of a tone frequency transducer and a tone pickup means for generating a signal responsive to a tone generated by the tone transducer for exerting control over the lamp and lamp fan.

The fiber optics bundle may be a separate unit for independent use in examinations and other procedures not requiring a dental drill.

All of the above techniques, in addition to totally eliminating the electrical connection between the lamp supply and the remote control unit, eliminate the need for a transformer, allowing use of a lamp having a 150 watt, 115 volt rating in place of a lamp having a 150 watt, 21 volt rating, which significantly reduces the size, weight, complexity and cost of the electrical components employed in the lamp source circuit.

OBJECTS OF THE INVENTION AND BRIEF DESCRIPTION OF THE FIGURES

It is, therefore, one object of the present invention to provide for the control of an electronic function at a location remote from the device being controlled and through wireless means.

Still another object of the present invention is to provide apparatus of the type described wherein the wireless means utilizes an electromagnetic carrier wave.

Still another object of the present invention is to provide apparatus of the type described wherein the wireless means comprises a sonic or ultrasonic wave.

Still another object of the present invention is to provide apparatus of the type described wherein the carrier comprises electromagnetic waves having a wavelength lying within the visible light spectrum.

Still another object of the present invention is to provide apparatus of the character described wherein a fiber optics bundle is utilized to convey a carrier of the visible light spectrum between the control unit and the device being controlled.

Still another object of the present invention is to provide apparatus of the character described wherein the signal operating means is automatically activated merely by lifting the device providing the light for the operator.

Yet another object of the present invention is to provide apparatus of the character described wherein an optically coupled isolator is employed as the coupling means between a battery powered circuit activated by manually operable switch and a control circuit responsive to the phototransistor provided within the optically coupled isolator for selectively turning on the illumination source for the fiber optics bundle, while isolating the lamp power source from the operator.

Still another object of the present invention is to provide apparatus of the character described above and employing an optically coupled isolator wherein logic means is provided within the control circuit for controlling the intensity level of the fiber optics bundle illumination source in accordance with the number of times the manually operable switch is activated.

Still another object of the present invention is to provide apparatus of the character described and employing an optically coupled isolator wherein similar control is exerted over a cooling fan for the fiber optics bundle illumination source.

Still another object of the present invention is to provide apparatus of the character described wherein sonic signal transducer and sonic pick up means are substituted for the aforementioned optically coupled ioslator.

Yet another object of the present invention is to provide apparatus of the character described wherein said switch is activated by the delivery of air under pressure to the dental handpiece in which the distal end of the fiber optics bundle is mounted.

The above, as well as other objects of the present invention, will be best understood from a consideration of the following detailed description and drawings in which:

FIG. 1a shows a sectional view of the remote control unit of FIG. 1 looking in the direction of arrows 1a—1a.

FIGS. 3d and 3e show still further preferred embodiments of the present invention employing battery powered electrical means for utilization in the remote control unit, wherein FIG. 3e further employs level control means of the type employed in FIGS. 3a—3c.

FIG. 3f shows still another embodiment of the present invention employing wireless carrier techniques.

FIG. 4 shows a perspective view of still another preferred embodiment of the present invention in which the remote control function is integrated into the dental handpiece.

FIG. 4a shows a sectional view of the switch portion of the handpiece of FIG. 4 looking in the direction of arrows 4a—4a.

FIG. 4b shows a detailed perspective view of the switch arrangement of FIG. 4.

FIG. 5 shows one typical dental unit for use in treating patients and the manner in which the apparatus of the present invention may be mounted with regard thereto.

FIG. 6 shows a simplified perspective view of a cradle for supporting a dental handpiece and for automatically activating the main light source.

FIG. 6a shows a simplified schematic of an electrical circuit which may be employed with the cradle of FIG. 6.

FIG. 7a shows a detailed block diagram of the phase shift control circuitry shown in simplified form in FIG. 7.

FIG. 7b shows an alternative embodiment of a magnetically coupled isolator which may be used in place of the optically coupled isolator of FIG. 7.

DETAILED DESCRIPTION OF THE INVENTION AND ITS PREFERRED EMBODIMENTS

Figure 1:
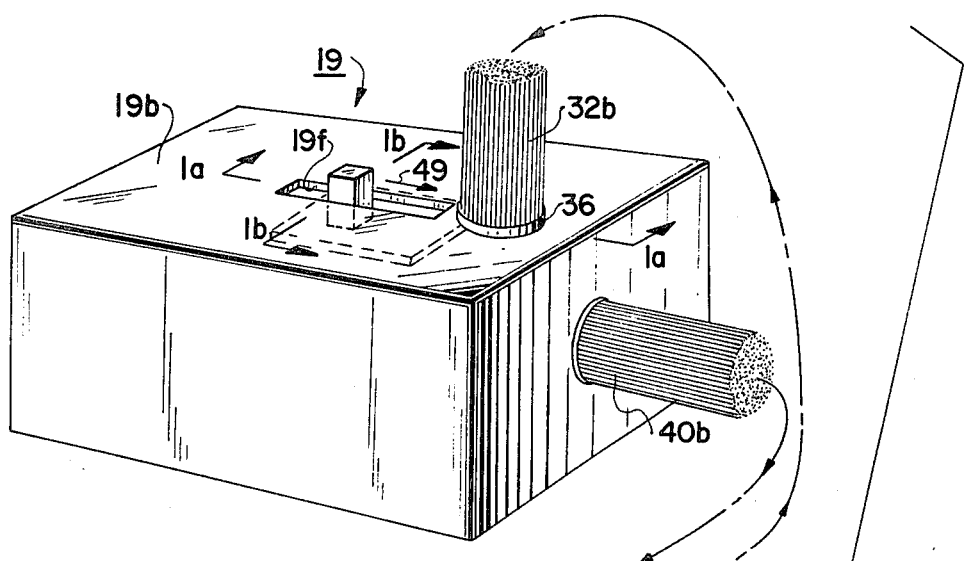
FIG. 1 shows a perspective view of a control apparatus designed in accordance with the principles of the present invention.

Turning initially to a consideration of FIG. 5, there is shown therein a patient unit 10 comprised of a pedestal 11 upon which chair 12 is mounted in a fashion so as to be both tiltable and swingable upon pedestal 11. A horizontally aligned arm 13 extends outwardly from pedestal 11 and to one side of chair 12. A vertically aligned post 14 is mounted upon the free end of arm 13 and has a swivel arm 15 pivoted thereto so as to swing about pivot point 15a. The free end of arm 15 is pivotally connected to a second arm 16 swingable about pivot point 16a so as to enable tray 17, mounted to the free arm of 16, to be positioned at a location convenient for the operator to place implements and materials utilized during a dental procedure without leving the patient's side. The housing 18 may be mounted on post 14 and is designed to house a variably intensity light source which is remote from the immediate work area, such mounting being acceptable through suitable mounting brackets or other securement means.

A remote control unit 19 is mounted upon tray 17 and is shown as being positioned immediately adjacent to the control panel 20a of a control housing 20 providing easy and immediate access for manipulation of the dials and/or switches associated with control functions normally required in the dental work area. The remote control unit is typically provided with switch means in the form of a manually operable knob 19a for turning the light source on or off and, in some preferred embodiments, for controlling the intensity of light emitted by the light source. In certain preferred embodiments, the remote control unit 19 is coupled to the light source receptacle 18 by a suitable electrical cable or conduit 21 which may be clamped on post 14 and arms 15 and 16 at spaced intervals, for example as shown by the clamping means 22.

The light source housed in receptacle 18 is preferably a lamp capable of utilizing conventional 115 volt AC power. Although not shown in FIG. 5 for purposes of simplicity, a blower is preferably provided within housing 18 for cooling the lamp. The blower is preferably turned on and off in conjunction with the lamp. Louvers 18a may be provided along one or more surfaces of the receptacle to aid in such cooling.

The lamp conveys light to the dental handpiece by means of a fiber optics bundle, the proximal end of the fiber optics bundle being positioned immediately adjacent the lamp housed within receptacle 18 and the distal end thereof being fixed to the handpiece so as to be in close proximity to the drill mounted within the handpiece, as is described in detail in the abovementioned U.S. Pat. No. 3,758,951, and as shown for example in FIG. 1 of the patent.

In another preferred arrangement, as shown herein in FIG. 4, the fiber optics bundle 23 may extend through the body of the handpiece 24 and be divided into first and second branches 23a and 23b whose distal ends 23a-1 and 23b-1 are positioned on opposite sides of the handpiece drill 25 so as to flood the region to be drilled with light.

Figure 1A:
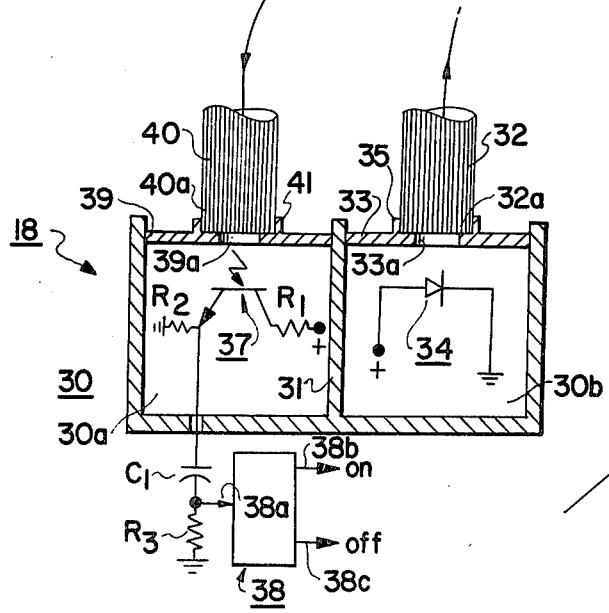
Figure 1B:
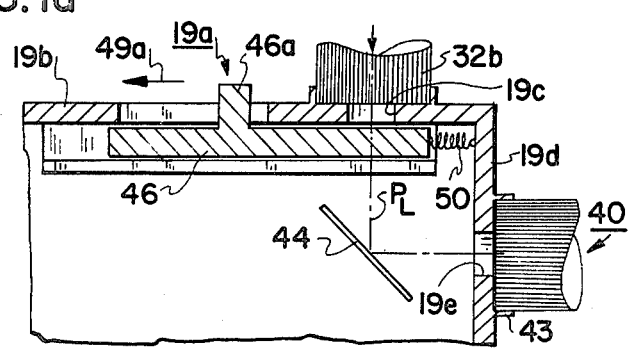
FIG. 1b shows a sectional view of the remote control unit of FIG. 1 looking in the direction of arrows 1b—1b.
Figure 1B:
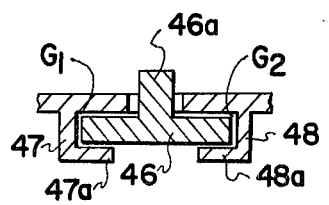

Considering FIGS. 1 through 1b, showing remote control unit 19 and a portion of receptacle 18, the apparatus for controlling "on" and turn-off of the lamp utilizes fiber optics bundles and operates in the following manner:

Receptacle 18 is provided with a separate small housing 30 divided into compartments 30a and 30b by barrier wall 31. A first fiber optics bundle 32 has its proximal end 32a secured by bracket 35 to one face of cover plate 33 having an opening 33a. Compartment 30b houses an LED 34 coupled between the positive terminal of a voltage source and ground potential as shown. The distal end of 32b of fiber optics bundle 32 is secured to the top surface of remote control unit 19 by suitable mounting means 36. Although not shown, it should be understood that the fiber optics bundle 32 may be housed within a separate protective sleeve. Thus, light emitted from LED 34 is conducted through fiber optics bundle 32 to remote control unit 19 and through the opening 19c in top surface 19b as shown best in FIG. 1a.

Chamber 30a houses a phototransistor 37 having its collector coupled to the positive terminal of a voltage source through resistor R1 and having its emitter coupled to ground through resistor R2. The emitter of 37 is also coupled to the trigger input 38a of a bistable flip-flop 38 through capacitor C1 whose opposite terminal is coupled to trigger input 38a and to ground potential through resistor R3.

The cover plate 39 of chamber 30a is provided with an opening 39a. The proximal end of fiber optics bundle 40 is secured to the upper face of cover plate 39 by mounting means 41. The distal end of 40b of fiber optics bundle 40 secured to one side face 19d of remote control unit 19 by a mounting bracket 43. Side face 19d is provided with an opening 19e.

The remote control unit 19 houses a reflective member 44 which reflects light entering into housing 19 from fiber optics bundle 32 toward fiber optics bundle 40 when an unobstructed light path is present. The condition of the light path is controlled by switch means 19a comprised of a slide member 46 having an upwardly extending manually operable projection 46a extending through elongated slot 19f in upper surface 19b.

The slide member 46 is slidably guided between two downwardly depending arms 47 and 48 each having inwardly directed flange portions 47a and 48a respectively forming slide grooves G1 and G2 which receive the opposite sides of slide member 46 as shown best in FIG. 1b. By moving projection 46a in the direction shown by arrow 49, the right-hand portion thereof extends into the path $P_L$ of light emitted from fiber optics bundle 32 so as to prevent light from reaching reflective member 44 so as to be directed toward the distal end of fiber optics bundle 40.

By moving the slide arm projection in the opposite direction as shown by arrow 49a, the right-hand end of slide member 46 moves out of the light path $P_L$ enabling light from fiber optics bundle 32 to impinge upon the reflective surface of member 44 so as to be directed into the distal end of fiber optics bundle 40 and thereby conveyed by bundle 40 to impinge upon phototransistor 37.

The current signal developed by phototransistor 37 is applied to the trigger input of the bistable flip-flop 38 causing its output terminals 38b and 38c to go high and low respectively. The high output at terminal 38b is utilized to turn on the lamp source in receptacle 13 to provide light of suitable intensity for the dental handpiece 24 as shown, for example in FIG. 4 of the present invention.

The switch may be automatically reset by coupling a suitable biasing spring 50 between the right-hand end of slide member 46 and the vertical side wall 19d requiring a subsequent opening of the switch turn-off of the light source. For example, by closure of the swtich under the control of spring 50, light no longer reaches phototransistor 37, causing the voltage level at its emitter to drop to reference potential. Bistable flip-flop 38 may be of the type which changes state only on a positive going edge and hence the negative going edge has no effect on its state. By operation of the switch at a later time, the next positive going edge causes flip-flop 38 to reverse its stable state whereby outputs 38b and 38c go low and high respectively to turn off the main lamp source. Obviously any other type of switching means may be provided, it being understood that the nature of the control established through the fiber optics is such as to totally eliminate the need for any electrical leads between the remote control unit 19 and receptacle 18.

Figure 2:
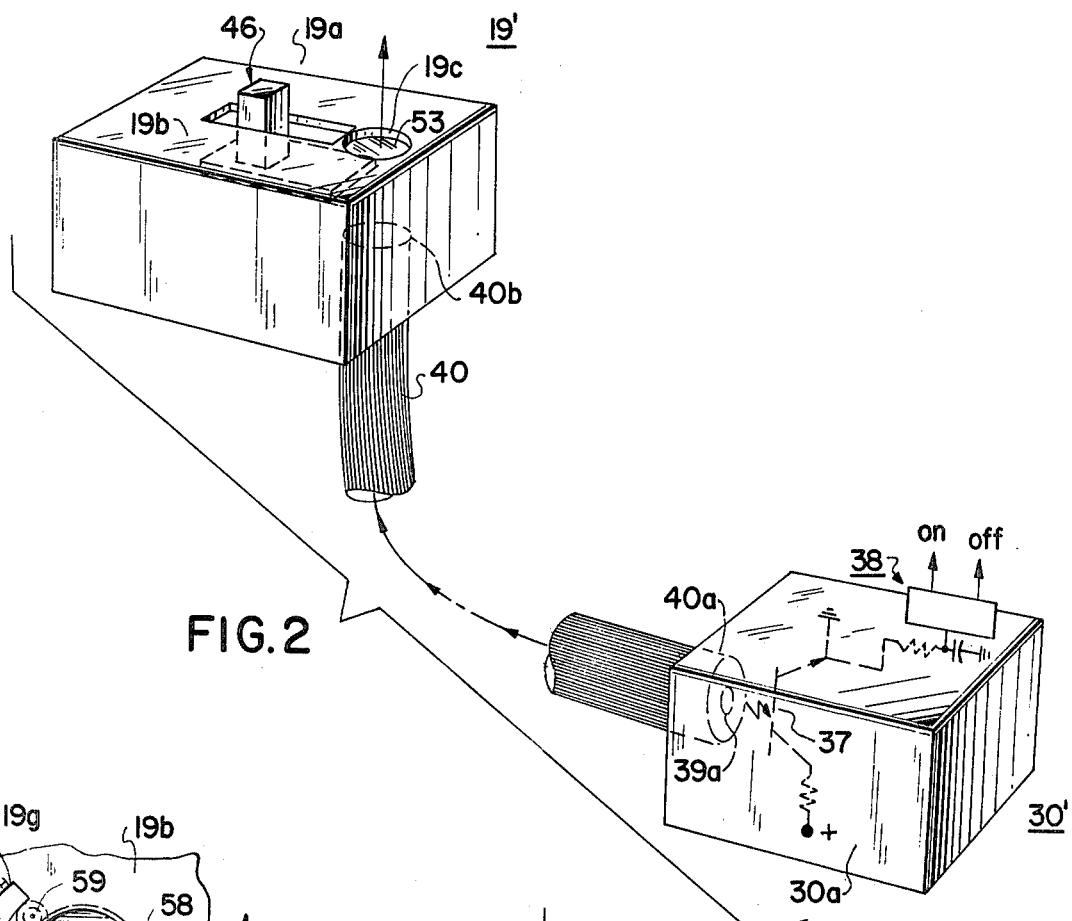
FIG. 2 shows a perspective view of another preferred embodiment of the present invention.

The arrangement of FIG. 2 eliminates the need for two fiber optics bundles and LED 34 by providing a remote control unit 19' which, although having a similar switch arrangement 19a, is provided with an opening 19c in its upper face 19b which is preferably fitted with a transparent lens member 53.

The separate chamber housing 30' provided in receptacle 18 is provided with a single chamber 30a housing the phototransistor 37. The opening 39a serves as a means to enable the passage of light from the proximal end 40a of fiber optics bundle 40 to the phototransistor 37. The distal end 40b of fiber optics bundle 40 extends into remote control unit 19' and is preferably positioned beneath and in close proximity to transparent lens 53. The similar switch arm assembly 46 is provided so as to position its right-hand portion between opening 19c and the distal end 40b of fiber optics bundle 40, or to be moved to a position displaced therefrom so as to enable ambient light passing through the transparent lens 53 to reach the distal end of fiber optics bundle 40 and be conveyed through the bundle 40 in opening 39a so that the light impinging upon phototransistor 37 causes generation of a signal for operating bistable flip-flop 38 in a manner similar to that described hereinabove. Since the dental area is normally well lighted, ambient light will be of a level more than sufficient to assure positive operation of the switching means. Thus, the embodiment of FIG. 2 performs the same switching function as the remote control unit of FIG. 1 while totally eliminating one fiber optics bundle and LED 34 as well as its powering means.

The embodiments described hereinabove serve to control the selective turn-on and turn-off of a remote electrical function. However, numerous applications exist wherein it is desirable to not only turn-on and turn-off the main lamp but to adjust its light intensity. FIGS. 3a through 3e teach embodiments for providing this capability.

Figure 3A:
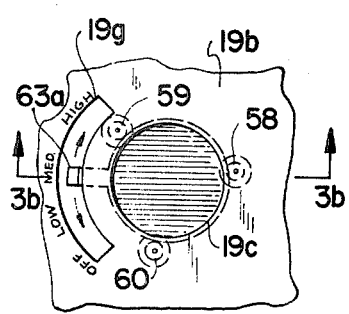
FIG. 3a shows a top plan view of a portion of another preferred embodiment of a remote control unit embodying the principles of the present invention.
Figure 3B:
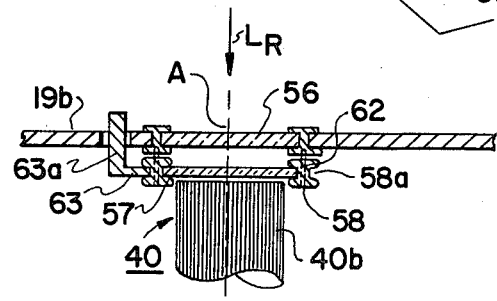
FIG. 3b shows a sectional view of the remote control unit of FIGS. 3a looking in the direction of arrows 3b—3b.
Figure 3C:
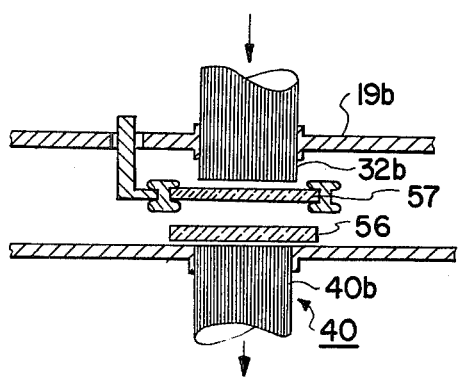
FIG. 3c shows sectional view of a modification of the remote control unit of FIG. 3a looking in the direction of arrows 3b—3b.

Turning initially to a consideration of FIGS. 3a and 3b, the top face 19b of the remote control unit is shown as having a circular opening 19c and an arcuate shaped slot 19g concentric with opening 19c. A polarized lens 56 is fitted in opening 19c. A second polarized lens 57 is rotatably mounted between three roller members 58, 59 and 60 arranged at 120° intervals about the axis of rotation A of polarized lens 57. Each of these rollers is provided with a groove, for example, roller 58 is shown as being provided with a groove 58a arranged around its cylindrical periphery to receive and support the marginal edge of polarized lens 57. A thin frame 62 encircles polarized lens 57 and has secured thereto an outwardly extending projection arm 63 whose free end 63a is bent upwardly so as to extend through arcuate shaped slot 19g to serve as the operating arm for the remote control means.

By moving the operating arm 63a either clockwise or counterclockwise, lens 57 may be rotated through an angle of 100° or more. This permits relative rotation between polarized lenses 56 and 57 to prevent light rays from the ambient light as represented by arrow $L_R$ from passing through the lenses and entering into the distal end 40b of fiber optics bundle 40. By rotation of lens 57 through a suitable angle from the position where the lenses provide an "opaque" condition, the amount of the ambient light passing therethrough may be controlled over a range which at one limit provides a substantially opaque condition and at the other limit provides a substantially transparent condition to thereby attenuate the light passing through fiber optics bundle 40 by an adjustable amount which may be utilized to cause a phototransistor to generate a current whose magnitude is a function of the intensity of light so as to control a servo-mechanism or other suitable device (not shown for purposes of simplicity) to convert the intensity of light and magnitude of current into a control value for controlling the intensity of light emitted by the main light source which illuminates the fiber optics bundles serving to illuminate the mouth of the patient, such as for example the fiber optics branches 23a-1 and 23b-1 of the dental handpiece 24 shown in FIG. 4 of the present invention. Obviously, suitable markings may be provided adjacent arcuate slot 19g for simplifying the adjustment of the operator to obtain the desired light intensity.

The embodiment shown in FIGS. 3a and 3b is designed to take advantage of ambient light. However, this embodiment may be altered in a manner shown in FIG. 3c to be utilized with the LED in phototransistor arrangement 34, 37 respectively of FIG. 1. This is accomplished by securing the distal end 32b of fiber optics bundle 32 in an opening (FIG. 3c) provided in the upper face 19b of the remote control unit. Thus light directed from LED 34 (see FIG. 1) is conveyed to the upper surface of polarized lens 57. Lens 56 is shown as being mounted in a stationary fashion beneath rotatable lens 57 with its bottom surface adjacent to the distal end 40b of fiber optics bundle 40. In all other respects, the embodiment of 3c functions in the same manner as the embodiment of FIGS. 3a and 3b. However, the use of a separate LED assures more accurate control over the level of light being attenuated as compared with the use of ambient light.

Figure 3D:
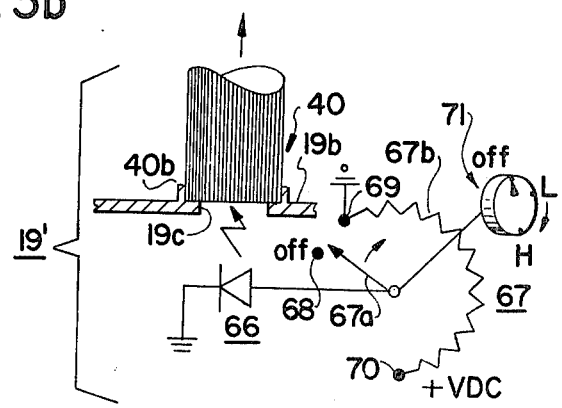

FIG. 3d shows still another alternative embodiment for the present invention wherein the remote control unit utilizes only one fiber optics bundle 40 having its distal end 40b secured above the opening 19c. An LED 66 is mounted within the remote control unit 19' and is electrically coupled between a reference potential and a potentiometer 67 comprised of a rotary switch arm 67a and a resistance element 67b adapted to be slidably engaged by the free end of switch arm 67a. One end of resistance element 67b is coupled to reference potential while the other terminal is coupled to a positive DC source which is preferably a small penlite battery or nickel-cadmium battery. By moving switch arm 67a from the stationary OFF contact 68 to the grounded contact 69, LED 66 remains deenergized. However, moving the rotary switch arm 67a in a clockwise direction between contact 69 and contact 70, reduces the ohmic value of the resistance coupled between LED 66 and the battery causing the intensity of the light emitted by the LED to continually increase. This operation may be performed by manual manipulation of the control knob 71 which is preferably mounted upon top surface 19b of the remote control unit. Thus, the arrangement of FIG. 3d provides a means for controlling both ON/OFF and light intensity by employing an LED mounted within the remote control unit together with a small battery. Since the LED 36 has a very low current drain, the battery need be changed very infrequently, for example, once per year. Also, there is no danger whatsoever of experiencing any shock as a result of the presence of a small low power battery in the remote control unit.

FIG. 3e shows an embodiment in which the LED arrangement of FIG. 3d may be combined with the polarized lens arrangement of FIGS. 3a and 3b. As shown therein, LED 66 may be coupled to the plus terminal of the DC source through a resistor R5 by simple closure of switch 72. Thus light is emitted through the polarized lenses 56 and 57 to enter the distal end 40b of fiber optics bundle 40. Light of a constant brightness is provided and the intensity of light is regulated by rotating polarized lens 56 relative to lens 57 in the same manner as the control apparatus shown in FIGS. 3a and 3b. Again the embodiment of FIG. 3e utilizes a small, low power battery within the remote control unit, which battery experiences low current drain due to the low current requirements of the LED 66.

FIG. 3f shows still another embodiment of the present invention wherein a positive DC source, which is preferably a penlite battery, is selectively coupled to a high frequency generator 76 by means of a normally opened switch 77. Switch 77 is normally biased to the open positioned by spring means 78. By depressing switch button 77a, movable arm 77b provides a shunt path across stationary contacts 77c and 77d to energize tone generator 76 which generates a constant frequency tone, the tone being transmitted over antenna 79 to a small receiver antenna 80 provided within the receptacle 18. The received signal is stepped down in frequency at 85, is amplified at 81, undergoes filtering by band-pass filter 82, and is again amplified at 83 which circuit further provides wave shaping of the signal to create a trigger signal for operating a bistable flip-flop 84 for turn on of the main lamp source referred to hereinabove.

The tone generator 76 generates a radio frequency wave picked up by a receiver 85 tuned to the proper frequency. Alternatively, the tone generator 76 may generate a signal in the audio range, preferably in excess of 20,000 cycles per second so as to lie above the normal hearing range. The signal may be generated by a constant frequency generator 75 and applied to a piezoelectric crystal element for converting the electrical signal into a sonic frequency. The receiver 80 is preferably a piezo-electric crystal utilized to convert the received audio frequency signal into an electrical signal which is again amplified, filtered and appropriately wave-shaped to control the bistable flip-flop 84, or for that matter, any other control circuit suitable for turning on and turning off the light source.

The main light source may be automatically activated merely by lifting the light carrying handpiece. For example, FIG. 6 shows the handpiece 24 (of FIG. 4) as being held by a cradle member 100 when not in use. The cradle member is bifurcated to receive the body portion 24a in slot 101 while the bifurcated arms 100a and 100b support the larger diameter head portion 24c.

As shown in FIG. 6a, the cradle may be pivotally mounted at a point 102 intermediate its ends, a spring 103 having a light spring force tends to urge the cradle clockwise about pivot 102. A microswitch 104 is connected between a voltage source +V and a transmitter 76 (see also FIG. 3f).

When the handpiece 24 is resting in the cradle 100, the weight of the handpiece overcomes the light spring force of spring 103 and rotates the cradle counterclockwise, causing the right-hand end of the cradle to urge the arm 104a of the microswitch contacts (not shown) in the open position. When the handpiece is lifted from the cradle, the spring 103 urges the cradle clockwise about pivot 102 to move the cradle arm away from the microswitch arm 104a causing the microswitch to couple source +V to transmitter 76 which operates in the same manner as was described in connection with FIG. 3f.

In place of a pivotally mounted cradle, the microswitch may be activated by insertion of the handpiece into a nesting opening (not shown) which is adapted to receive and support the handpiece 24 when not in use. The microswitch may be activated when the handpiece is inserted and/or removed from the nesting socket.

The microswitch may be replaced by a switching technique of the type shown in FIGS. 4–4b, wherein the cradle may be provided with a projection movable between the adjacent ends of two fiber optics bundles to couple light from a light source to a phototransistor for activating the main light source.

As still another alternative embodiment for the present invention, the capability of the remote control unit may be directly built into the dental handpiece as an integral part thereof or, alternatively, may be strapped to or otherwise affixed to the handpiece, preferably at a location which does not interfere with the holding and manipulation of the handpiece so as to avoid accidental turn-on or turn-off of the light source. Alternatively the handpiece may comprise only a light source usable alone or with a drill handpiece by being strapped or otherwise secured to the dental drill handpiece.

As shown in FIGS. 4 through 4b, the handpiece is provided with an elongated body portion 24a having a coupler 24b at its lower end for coupling the drive air, water, exhaust and fiber optics bundle 23 extending from their sources to the handpiece 24 as is conventional in such prior art apparatus.

In addition thereto, the handpiece of the present invention provides coupling for two additional fiber optics bundles 32 and 40 which extend into the bottom portion of handpiece 24. The lower end of the handpiece body 24a is fitted with a manually operable slide button 90. The surface thereof is roughened or otherwise provided with a plurality of V-grooves 90a to facilitate simple movement of the slide button between an ON and an OFF position. As shown, for example in FIGS. 4a and 4b, the interior side of the slide button 90 which extends into body 24a is provided with a pair of L-shaped flanges 91 and 92 which define grooves 95a and 95b adapted to slidably receive the marginal edges of an opening 95 in handpiece body 24a so as to permit the slide button to be reciprocally movable along the handpiece body. A sheetlike projection 97 extends from the interior surface of slide button 90 into the body of the handpiece so as to be movably positioned between the distal ends 40b and 32b of the fiber optics bundles 40 and 32 respectively. Thus, as shown in FIGS. 4 and 4b, when slide button is moved to its uppermost (OFF) position, the sheetlike projection 97, which is preferably opaque, extends between the distal ends of fiber optics bundles 40 and 32 to prevent light from passing therebetween. By moving slide button from the OFF position and downwardly in the direction shown by arrow 99, the plate-like projection 97 is moved from its position between the distal ends 40b and 32b of the fiber optics bundles 40 and 32 to permit light conveyed toward the distal end of fiber optics bundle 32 (for example from the LED 34 shown in FIG. 1) to enter the distal end 40b of fiber optics bundle 40 so as to be conveyed, for example, to phototransistor 37 shown in FIG. 1 so as to enable remote operation of the main light source conveying light to the fiber optics branches 23a and 23b, to be controlled directly from the dental handpiece thereby totally eliminating the remote control unit. Obviously, if desired, the fiber optics bundle 32 may be eliminated and ambient light may be utilized in the embodiment shown in FIGS. 4–4b by using the technique described in connection with the embodiment of FIG. 2. Also the alternative arrangements for providing intensity control and/or a localized power source at the dental handpiece may also be incorporated therein (i.e., a penlite battery). However, it is most desirable to maintain the handpiece as trim and uncluttered as is possible so that the preferred arrangement therefore is that shown in FIGS. 4 through 4b.

Figure 7:
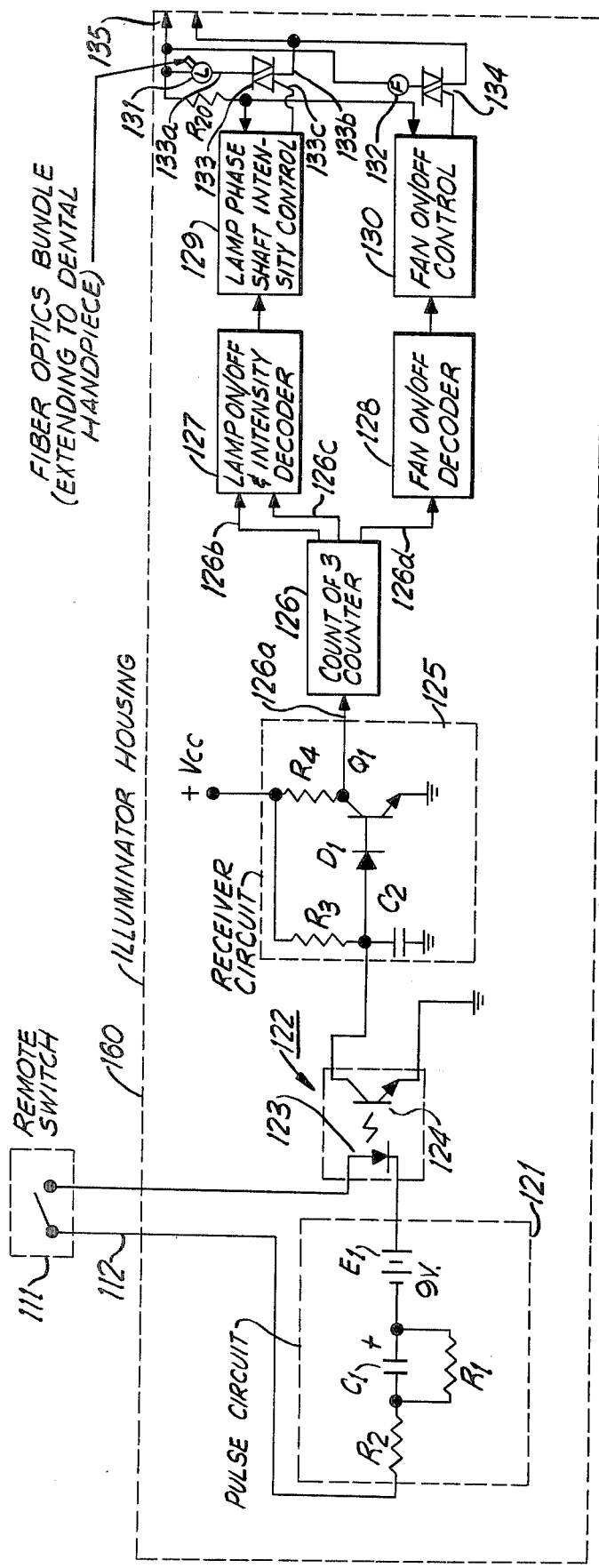
FIG. 7 shows a block diagram of another embodiment of the control means.
Figure 8:
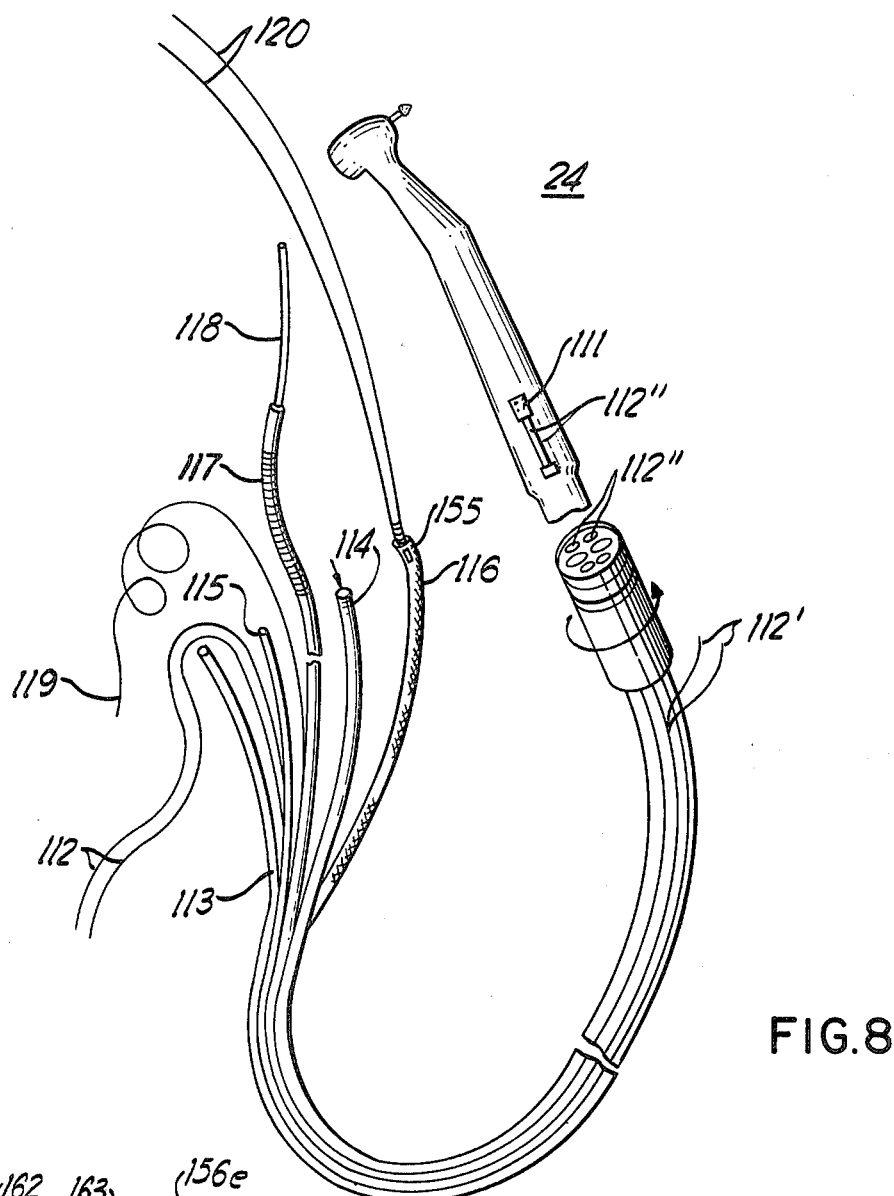
FIG. 8 shows a dental handpiece assembly which may be operated by the control circuitry of FIG. 7.

Turning to a consideration of FIG. 7, there is shown therein still another preferred embodiment 110 of the present invention which is comprised of a miniature size switch 111, preferably of the normally-open type pushbutton and which is adapted to be mounted either directly upon or in close proximity to the dental handpiece (see FIG. 8). A pair of elongated leads 112 serve to couple the remote switch 111 into the activating circuit to provide automatic control of the lamp as will be more fully described.

Considering FIG. 8, the aforementioned pair of lead lines 112 is combined in a single bundle with the other conduits which serve as the means for conveying light, pressurized air, water and so forth to the handpiece.

Typically, the handpiece 24 may be coupled with a bundle of conduits such as the water 113, air 114, chip air 115, and exhaust 116 conduits as well as a fiber optic cable 117 in which is mounted the fiber optics bundle 118. A strain relief cord 119 may also be provided to prevent any of the individual conduits, cables, lead lines and the like from being stretched or broken.

Exhaust conduit 116 may be provided with a pressure transducer or pressure sensitive switch 155 mounted within conduit 116 and coupled to suitable circuit control means by lead lines 120. The pressure transducer or pressure sensitive switch 155 is rendered operative in the presence of air under pressure within the exhaust conduit 116 for the purpose of controlling lamp 131 as will be more fully described.

The lead lines 112 may extend to a position just below the handpiece coupling member 24C as shown at 112' or, alternatively may extend through coupling 24C as shown at 112" and may extend into the handpiece 24 as shown at 112''', enabling the switch 111 to be mounted directly upon handpiece 24. Alternatively, the remote switch 111 may be mounted at or just below the handpiece coupling 24C which is also a convenient location for manipulation by the operator.

The bundling of the lead lines 112 in the manner shown does not in any way complicate the design of the handpiece or its conduits and further serves to prevent the lead lines for switch 111 from interfering in any way with the physical positioning, movement or functioning of the handpiece and the conduits servicing the handpiece.

Turning to a consideration of FIG. 7, remote switch 111 is shown as being connected in electrical series with pulse circuit 121 and the light emitting diode element 123 provided within the optically coupled isolator 122.

The optically coupled isolator 122 is, in one preferred embodiment a small, fully self-contained package comprised of an enclosure having lead lines extending through the body of the enclosure for facilitating its connection in an electrical circuit and housing in its interior a light emitting diode 123 and a phototransistor 124. One suitable device of this type is the 4N25 optically coupled isolator which may be obtained from Optron Inc. and having a light emitting diode 123 of the gallium arsenide infrared type and having a silicon type phototransistor 124.

As shown in FIG. 7, the light emitting element 123 is connected in the electrical circuit loop including remote switch 111 and pulse circuit 121. Pulse circuit 121 is comprised of parallel connected resistor and capacitor R1 and C1, respectively. A resistor R2 is connected in series with the parallel connection while a power source E1, which in the present example is a small size 9 volt battery, is utilized as the low voltage power source for the pulse circuit.

Momentary closure of remote switch 11 causes a pulse to be instantaneously applied to the light emitting element 123, said pulse instantaneously building to the voltage of source E1, and decaying at a rate determined by the value of the circuit components R1, C1 and R2.

The aforementioned generated pulse causes the light emitting dioe (LED) 123 to conduct and thereby emit light (in the infrared wave length in the example given). This light is detected by phototransistor 124 whose conductivity increases as a function of the intensity of infrared light impinging thereon.

The conductor-emitter electrodes of phototransistor 124 are connected across the terminals of capacitor C2 forming a part of receiver circuit 125. Receiver circuit 125 is further comprised of a transistor Q1 which has its collector connected to a positive DC source +Vcc through resistor R2 while its emitter is connected to ground. A charging resistor R3 connects capacitor C2 to source +Vcc and the common terminal between R3 and C2 is connected to the base electrode of Q1 through diode D1. During the time that phototransistor 124 is nonconductive, capacitor C2 charges to the level +Vcc causing transistor Q1 to conduct so that its collector electrode is substantially at ground potential.

When remote switch 11 is closed, causing emitting element 123 to be pulsed with electrical energy, the infrared light emitted from LED 123 substantially increases the conductivity (i.e., substantially reduces the resistivity) of phototransistor 124 to ground. The abrupt reduction in the voltage level at the common terminal between R3 and C2 serves to turn transistor Q1 off causing the voltage level at the collector of Q1 to move abruptly toward the supply level +Vcc. This positive going pulse is applied to the trigger input 126a of a counter 126. In the preferred embodiment, counter 126 is provided with two stages and is electrically hand-wired so as to be capable of counting up to a count of 3 and then automatically resetting the counter thus repetitively producing the binary outputs (00), (01), (10), (00), (01), (10). One typical way of providing the desired circuitry is through the employment of an integrated circuit, for example of the type 4027 whch is comprised of first and second J-K master/slave flip-flops. One suitable integrated circuit of this type is the CD 4027 Ad digital integrated circuit produced by the Solid State Division of RCA.

The control signal utilized for purposes of controlling off, on and lamp intensity level are taken from one output of each 126b and 126c of the two stages (i.e., flip-flops) comprising counter 126. In order to operate the fan, a third output 126d of the second stage is utilized. A description of the manner in which the output signals of the counter 126 are employed to control turn-on and intensity level of the lamp and turn-on and turn-off of the blower is set forth hereinbelow in greater detail.

The outputs 126b and 126c are coupled to a on/off and intensity decoder circuit 127. An on/off decoder circuit 128 for the fan is connected to output 126d.

Decoder 127 is coupled to a lamp phase shift intensity control circuit 129 while decoder 128 is coupled to a similar type circuit 130 for controlling selective energization of fan 132.

Lamp 131 and fan 132 are connected in a circuit loop with AC source 135 and triacs 133 and 134, respectively.

The triacs 133 and 134 are three-terminal devices. Two of the terminals (133a and 133b) may be likened to anode and cathode electrode while the third terminal (133c) is a gate electrode. Each triac will conduct when the voltage across its anode-cathode electrodes (133a and 133b) is greater than zero and when pulsed at its gate electrode such that the direction of the pulse applied at the gate electrode and the polarity of voltage across terminals 133a and 133b determines the direction of current flow. As a result, triacs 133 and 134 can be seen to be bidirectional devices with the anode and cathode electrodes 133a and 133b being interchangeable and functioning as cathode and anode electrodes during one half cycle and as anode and cathode electrodes during the next succeeding half cycle of the alternating current signal from source 135. Thus, if the gate electrode 133a is pulsed at the beginning of each half cycle, triac 133 will turn-on and remain on throughout that half cycle. However, as soon as the alternating current wave form passes through zero so that the voltage levels at the anode and cathode electrodes are reversed, triac 133 will no longer conduct unless another gate pulse of the proper polarity is applied to gate 133c at the inception of or at some point during the inception of the next half cycle of the AC signal. The gate pulse may occur at any time during each half cycle. If each gate pulse is caused to occur upon the initiation of each half cycle, i.e., as each half cycle passes through zero voltage in the positive going direction, triac 133 may remain on for 100% of each cycle of AC signal. However, by delaying application of each gate pulse a predetermined time after initiation of each half cycle it is possible to regulate the portion of each half cycle during which triac 133 is turned on.

These characteristics are utilized to advantage in the present invention by regulating the turn-on time of the triac during each half cycle of the AC signal, in accordance with the count present in counter 126 to either turn-off lamp 131, turn-on lamp 131 at half intensity or turn-on lamp 131 in full intensity, respectively.

The manner in which this is accomplished is by means of the decoder and phase shift intensity control circuitry shown in greater detail in FIG. 7a. As shown therein, the on/off and intensity decoder 127 is comprised of operational amplifier 137 having an inverting input coupled to output 126b of counter 126 through diode D2 and having a noninverting input coupled to output 126c of counter 126. The output of operational amplifier 137 is coupled to the noninverting input of the amplifier through resistor R5. The output of the operational amplifier is also coupled to the input of comparator 138 forming a part of the lamp phase shift and intensity control circuit. The circuit 129 further includes a zero crossing detector 139, ramp generator 140, zero current detector 141, control logic circuit 142, chopper circuit 143, output logic state circuit 144 and gate pulse stage 145.

The zero-crossing detector circuit 139 is coupled to the AC source 135 which serves to power lamp 131 as well as fan 132. Each time circuit 139 detects a zero crossing, its output 139a triggers ramp generator 140 to develop a ramp signal at its output 140a. This signal is compared by comparator 138 against the level appearing at the output of operational amplifier 137. When the ramp signal developed at output 140a reaches the voltage level applied to comparator 138 by operational amplifier 137, control signals are developed at outputs 138a and 138b of comparator 138. The zero-crossing detector also determines the polarity of each gate pulse signal and is coupled to control logic 142 for this purpose.

Zero-current detector circuit 141 is connected in series with AC source 135 and lamp 131 through resistor R7 to monitor the current through lamp 131. When the current through lamp 131 falls to zero, output 141a applies an enabling signal to control logic 142. Control logic circuit 142 which includes gatings means (not shown for purpose of simplicity) serves to develop an output pulse. Three conditions occur simultaneously, i.e., when there is no current flowing through lamp 131, when the AC wave form has made a zero crossing, and when the signal level ramp generator 140 has been reset and has increased to the level applied to comparator 138 by operational amplifier 137. The square pulse developed by control logic 142 is applied to chopper circuit 143 through capacitor C6 which converts the square pulse into an impulse signal. The output 138d of comparator coupled to chopper 143 prevents spurious gate pulses from forming before the comparator has switched correctly. The impulse signal appearing at output 143a is applied to output logic stage 144 which develops an output signal so long as a zero-crossing conductor is present. The output signal from the output logic stage 144 undergoes pulse shaping at gate pulse stage 145 to provide a sharp pulse of the proper polarity for application to the gate electrode 133a of triac 133. The manner of operation is such that when counter 126 is at a count of zero the control level applied to input 138a of comparator 138 through operational amplifier 137 is sufficiently high to prevent the ramp signal from reaching that level during each half cycle so as to keep lamp 131 in the off condition.

By closing switch 111, the count in counter 126 is advanced by one count (i.e., to 01) to develope a signal level applied to input 138a of comparator 138 by operational amplifier 137 to turn-on triac 133 after a delay subsequent to each zero crossing which is sufficient to illuminate lamp 133 at half intensity.

A subsequent momentary closure of switch 111 causes counter 126 to be advanced by one count to a count 10 causing the output level applied by operational amplifier 137 to input 138a of comparator 138 to be reduced below the aforesaid half intensity level whereby the signal developed by ramp generator 140 builds to the signal level at input 138a at a time still closer to the last occurring zero crossing to cause the gate of the triac to be pulsed at a closer point in time to the beginning of each half cycle to increase the one time of the lamp during each AC half cycle sufficient to cause the lamp to glow at fully intensity.

By closing remote switch 111 once more, counter 126 is automatically reset to a count of "zero" (00) returning the lamp 131 to the off condition by developing a signal level at input 138a high enough to prevent the ramp signal from reaching the level at input 138a during each AC half cycle.

The on/off decoder 128 and the fan on/off control 130 may be comprised of the same type of circuitry as that utilized for the lamp decoder 127 and lamp pulse shift intensity control 129, except that the fan on/off control and decoder is preferably connected to cause the fan to be operated at its full rated output regardless of the fact that the lamp is on at either full or half intensity. The circuitry which may be employed for the decoder and triac phase shift control is the L120 integrated circuit for triac phase control available from SGS-ATES.

The arrangement of FIG. 7 may be simplified by replacing count of 3 counter 126 by a count of 2 counter, i.e., by a bistable fip-flop, which is driven to one of its two stable states by closure of switch 111 and which is driven to the other of its two stable states by a subsequent closure of switch 111, wherein these states are utilized for turning off lamp 131 and for turning on 131 to fully intensity, respectively.

Obviously the opposite capability may likewise be provided wherein count of 3 counter 126 may be replaced by counter means having a capability of counting to greater than 3 counts in order to provide levels of intensity other than half intensity and full intensity as was set forth hereinabove.

As still another alternative to the embodiment described hereinabove, the optically coupled isolator may be replaced by a transducer capable of generating an audio frequency and a receiver element adapted to generate an electrical signal responsive to operation of the transducer element at the frequency of the transducer.

FIG. 7b shows still another alternative embodiment wherein the optically coupled isolator may be replaced by a reed switch assembly 150 comprised of a pair of switch elements 152 encapsulated within an evacuated envelope 153 and adapted to be maintained in the normally open position. The reed switch assembly is further comprised of a winding 151 wound about envelope 153 and electrically connected within the circuit loop including remote switch 111 and pulse circuit 121. Upon momentary closure of switch 111, winding 151 is pulsed to set up a magnetic field whch causes momentary closure of reed switch contact elements 152. By connecting these reed switch contact elements across capacitor C2, shown in FIG. 7, capacitor C2 may be caused to discharge through the closed reed switch elements to pulse counter 126 in the same manner as previously described with respect to the phototransistor 124 of the optically coupled isolator 122. It should be understood that the embodiment of FIG. 7 accomplishes all of the advantages of previously described embodiments of the present invention in that all of the elements shown in FIG. 7, with the exception of the remote switch 111 and its lead line 112, may be housed within a single housing presented by dashed line 60. The assembly is provided with a single power cord which may be coupled to a conventional 115 volt AC 60 Hertz power source which is wired to provide the power for driving lamp 131 and fan 132. The aforementioned integrated circuit type L120, further includes the capability of rectification and filtering of the AC signal to provide the DC levels necessary for powering transistor Q1 and counter 126, as well as the DC powdered circuits of decoder 127 and the shift control circuit 129, which circuits are shown in FIG. 7A. In addition, the circuit of FIG. 7 totally eliminates the need for an expensive and heavy transformer and for a special purpose lamp, which elements are required in the prior art design of U.S. Pat. No. 3,758,951, described hereinabove. The last described embodiment is quite compact, having a housing which occupies a small amount of space.

Figure 8A:
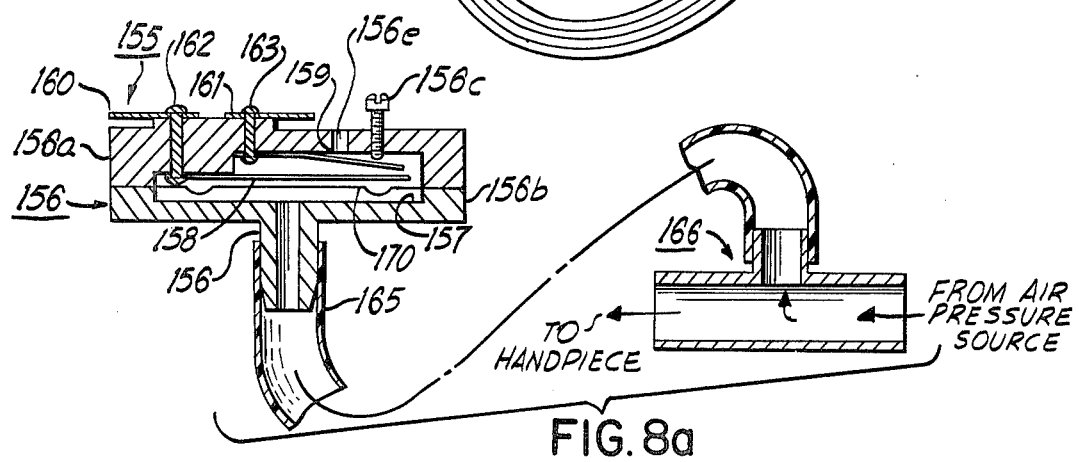
FIG. 8a shows a pressure sensitive switch which may be used to control turn-on and turn-off of the lamp.

FIG. 8a shows a pressure actuated switch assembly 155 which is advantageous for use in the present invention. The switch is comprised of enclosure halves 156a and 156b forming enclosure 156, having a hollow interior 157 for mounting resilient blades 158, 159 connected to electrical terminals 160, 161 respectively, through conductive pins 162, 163. Screw 156c adjusts the exposure of an aperature 156e in housing to control the pressure sensitivity. Hollow pressure port 156d receives air under pressure through a flexible conduit 165, coupled to drive air conduit 114 (FIG. 8) through T-connector 166. Diaphragm 170, which is sandwiched between enclosure halves 156a and 156b, moves upwardly against cantilevered contact 158 to close the switch.

When the operator depresses the pressure delivery switch, not shown for purposes of simplicity, air pressure is introduced into drive air conduit 114. The dental handpiece is typically provided with an impeller rotated by the drive air to operate a drill mounted at the working end of the dental handpiece. The drive air conduit 114 extends to one end of the impeller while the exhaust air conduit is placed on the downstream side of the impeller and carries exhaust air away from the dental handpiece to avoid an undesirable pressure drop at the impeller.

The pressure activated switch 155 is mounted within the exhaust air conduit 116 and closes when air under pressure is delivered to the dental handpiece 24. Switch closure may activate the pulse circuit 121 of FIG. 7 to selectively energize lamp 131 and fan 132 in the manner previously described.

The switch may alternatively take the form of a transducer which generates an electrical signal for activating one of the transmitting devices 123, for example, for controlling lamp 131 and fan 132.

Figure 9:
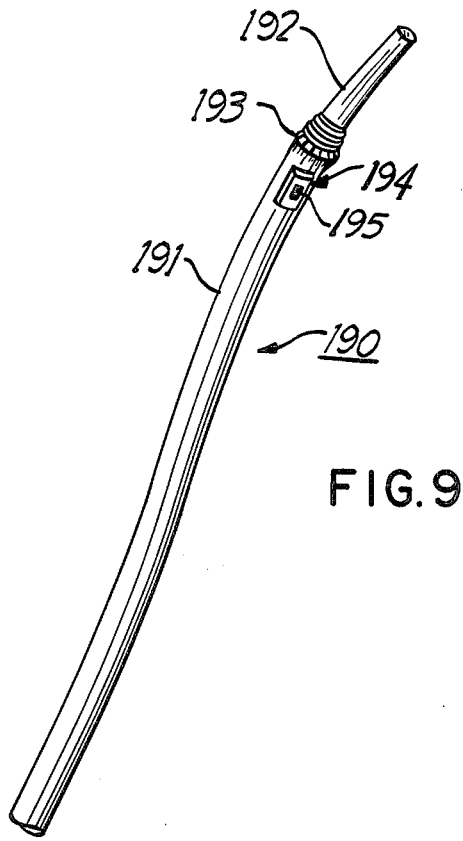
FIG. 9 is a perspective view of a stand alone fiber optics illuminator embodying the principles of the present invention.

FIG. 9 shows a fiber optics illuminator which may employ the remote switching capability of the present invention and which is an independent unit, as opposed to being integrated in a dental handpiece. The unit 190 is comprised of an elongated sleeve 191 whose lower end is shown broken but is understood to be positioned adjacent to the lamp source 131, for example, as shown in FIG. 7.

The sleeve 191 houses a bundle of optical fibers which are separate from one another to allow the sleeve to bend through rather small bending radii to facilitate manipulation and positioning of the unit.

The upper end 192 of the bundle is comprised of said optical fibers which have been potted in a transparent epoxy and then polished.

Elongated helical spring 193 serves to prevent undue bending of the upper end of the illuminator 190.

A switch 194 having a depressible member 195 is arranged below spring 193. By depressing member 195 the switch contacts (not shown) are closed. The contacts may be similar to those shown schematically as switch 111 in FIG. 7.

Figure 10:
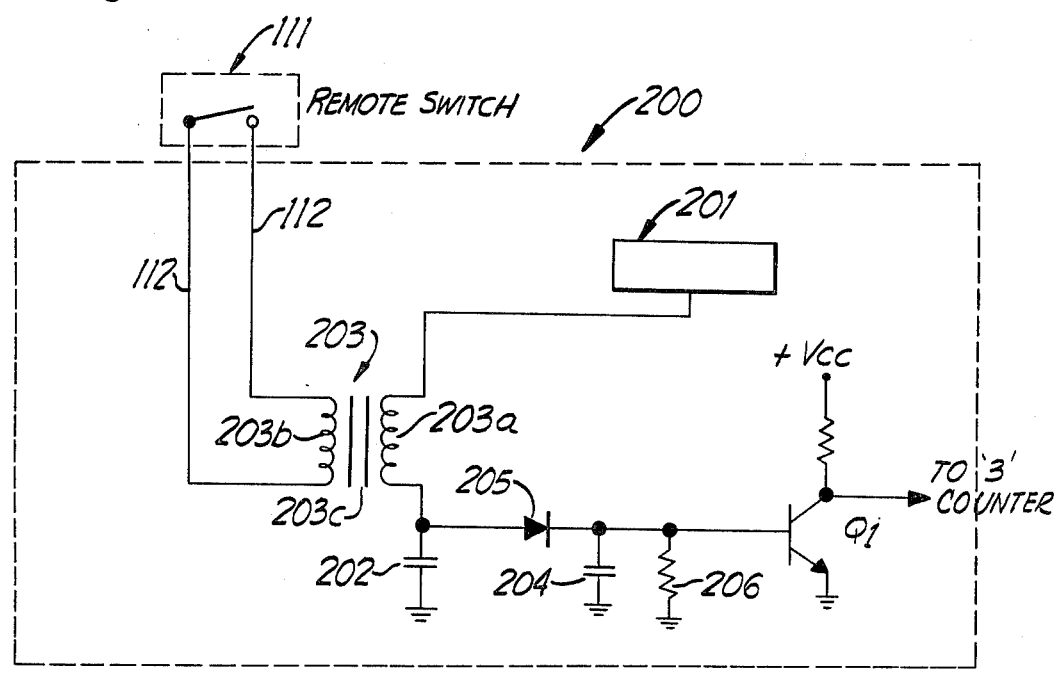
FIG. 10 shows a schematic diagram of another isolator circuit which may be employed to couple the remote switch of FIG. 7 to the count of three counter of FIG. 7.

FIG. 10 shows another electrical isolation technique which may be substituted for the optical isolator 122 shown in FIG. 7.

The circuitry 200 shown in FIG. 10 is comprised of a low voltage 10kHz signal generator 201 coupled to capacitor 202 through the one winding 203a of a transformer 203. The transformer further includes a winding 203b tightly inductively coupled to winding 203a by transformer core 203c. The end terminals of winding 203b are coupled to remote switch 111 through conductive leads 112 which may extend through sleeve 191 of the illuminator 190 shown in FIG. 9.

The closing of remote switch 111 alters the impedance of winding 203a by providing a direct short circuit condition across winding 203b. The short circuit condition across winding 203b is reflected back to winding 203a thereby greatly increasing the charging current to capacitors 202 and 204. Diode 205 prevents capacitor 204 from discharging back to either capacitor 202 or the oscillator 201. Thus, capacitor 204 can only discharge through resistor 206 whch has a high ohmic value (of the order of 100k ohms) so that capacitor 204 discharged slowly.

When capacitor 204 charges to a sufficient level Q1 is turned on to operate the count of 3 counter in the same manner as was previously described wth regard to FIG. 7.

The signal developed by oscillator 201 is insufficient to cause any shock or injury to an operator especially due to its low voltage rating, and further avoids the need for a separate battery since oscillator 201 may be powered by rectifying and filtering line voltage down to a level of the order of 5 volt d.c., or less.

What we claim is:

1. Control means for a fiber optic illumination system having a light source and a fiber optics bundle whose proximal end is positioned adjacent to said light source and whose distal end is positionable in the immediate region where an examination procedure is being performed to provide increased acuity in the region to be illuminated, said control means comprising a control unit small enough not to interfere with the normal use of other implements being employed in the work area;

signal generating means contained within said portable control unit including manually operable switch means for activating said signal generating means to create a function control signal;

sensing means for generating an activating signal upon receipt of said function control signal;

means connected to said sensing means for assuming at least first ans second states, said means for assuming responsive to a receipt of said activating signal to assume a predetermined one of said at least first and second states and retain such state until a subsequently generated activating signal is received; and means responsiveto said predetermined one state for applying energizing potential to said light source.

2. The apparatus of claim 1 wherein said signal generating means generates an electromagnetic wave and said sensing means comprises means for receiving said electromagnetic wave and converting said electromagnetic wave into said activating signal.

3. The apparatus of claim 2 wherein said electromagnetic wave has a wavelength which lies in the visible frequency range.

4. The apparatus of claim 2 wherein said electromagnetic wave lies in the frequency spectrum of visible light; and further comprising a second fiber optics bundle extending between said signal generating means of said remote control unit and said sensing means for conveying said electromagnetic signal.

5. The apparatus of claim 3 wherein a second elongated fiber optics bundle is provided;

a first end of said second fiber optics bundle being positioned adjacent said signal generating means while the opposite end of said fiber optics bundle is positioned adjacent said sensing means whereby the signal of the aforesaid wavelength of light is conveyed from said signal generating means to said generating means.

6. The apparatus of claim 3 wherein said signal generating means comprises a light source and said sensing means comprises a light sensitive element.

7. The apparatus of claim 6 wherein said light source is a light emitting diode and said sensing means is a phototransistor.

8. The apparatus of claim 1 wherein said signal generating means comprises means for generating an electrical signal of a signal frequency in the audio range;

transducer means for converting the electrical signal into a sonic wave;

said sensing means comprising transducer means responsive to receipt of said sonic wave for converting same into an electrical signal; and filter means for passing electrical signals lying within a narrow predetermined frequency range.

9. The apparatus of claim 6 wherein said signal generating means includes a miniature DC battery.

10. The apparatus of claim 1 wherein said signal generating means comprises means for generating a radio frequency signal and miniature antenna means for transmitting said radio frequency signal; and said sensing means comprises an antenna for picking up the aforesaid radio frequency signal, filter means for passing only those received signals lying within a narrow predetermined frequency range, and means responsive to those received signals passed by said filter means for generating said activating signal.

11. The apparatus of claim 1 wherein said sensing means comprises a light sensitive element;

a second source of light provided adjacent to said light sensitive element;

means for preventing stray light from said second source of light from reaching said light sensitive element;

a second fiber optics bundle extending between said second source of light and said control unit;

a third fiber optics bundle extending between said signal generating means and said light sensitive element;

said signal generating means comprising switch means for enabling light conveyed from said second source of light to said remote control unit by said second fiber optics bundle to be directed into said third fiber optics bundle so as to be conveyed from said control unit to said light sensitive element whereby said light sensitive element is activated to generate said signal.

12. The apparatus of claim 1 wherein said sensing means comprises a light sensitive element;

and further comprises a second fiber optics bundle extending between said portable control unit and said light sensitive element; and said switch means comprises means for selectively covering and uncovering the end of said fiber optics bundle in said portable control unit whereby when said second fiber optics bundle is uncovered, ambient light is conveyed through said fiber optics bundle to said light sensitive element for generating said activating signal.

13. The apparatus of claim 1 wherein said signal generating means comprises a miniature battery element;

a miniature light source; switch means for selectively coupling said light source to said battery; said sensing means comprises light sensing means; and an elongated fiber optics bundle extending between said miniature light source and said light sensing means for conveying light from said light source to said light sensing means when said switch means is operated to couple said battery to said light source.

14. The apparatus of claim 12 wherein said switch means is further comprised of a pair of mutually rotatable polarizing lenses for attenuating the amount of ambient light conveyed to said light sensitive element;

said light sensitive element comprising phototransistor means for generating a current signal magnitude which is a function of the light intensity it receives; and means responsive to the magnitude of the current signal for controlling the brightness of said main light source.

15. Apparatus for selectively controlling the energization of a lamp employed in a fiber optics system for providing light in a dental apparatus, said dental apparatus comprising a handpiece adapted for coupling with a motive power source to perform drilling and similar functions, comprising a first fiber optics bundle extending between said lamp and said handpiece whereby the distal end of said fiber optics bundle is positioned adjacent the end of said handpiece performing said drilling function so as to direct light towards the region to be operated upon by the working end of said handpiece;

signal generating means locatted near the end of said handpiece opposite said operating end;

light sensing means positioned remote from said handpiece and adapted when light is sensed to generate an activating signal for operating said lamp:

a second fiber optics bundle extending between said signal generating means and said light sensing means:

said signal generating means being adapted to generate a signal having a frequency in the visible wave length whereby said signal is conveyed through said second fiber optics bundle to cause said light sensing means to generate an activating signal; and means responsive to said activating signal for energizing said lamp.

16. The apparatus of claim 15 further comprising a third fiber optics bundle for conveying light from a second light source provided remote from said handpiece and in the region of said lamp to said signal generating means;

said signal generating means comprising switch means for selectively coupling light conveyed to said handpiece by said third fiber optics bundle to enter said second fiber optics bundle and be conveyed to said light sensing means for causing generation of said activating signal.

17. The apparatus of claim 13 wherein said switch means comprise a slidable switch button;

the distal ends of said second and third fiber optics bundle extending to said handpiece being positioned in close proximity to one another;

an opaque wall member movable by said slide member between a first position extending between the distal ends of said second and third fiber optics bundles and a second position displaced therefrom so as to couple light emitted from the distal end of said third fiber optics bundle to enter into the distal end of said second fiber optics bundle.

18. The apparatus of claim 1 further comprising a dental handpiece supporting the distal end of said fiber optics bundle;

said switch means comprising means for supporting said dental handpiece when not in use; and said supporting means includes means for automatically activating said switch means when said dental handpiece is lifted from said supporting means.

19. Control means for a fiber optic illumination system having a light source and a fiber optics bundle with a proximal end positioned adjacent to said light source and a distal end positionable in the immediate region where light is desired, said control means comprising:

a control unit whose small size enables the control unit to be positioned so as not to interfere with the normal use of other implements being employed in the dental work area and having signal generating means including switch means for activating said signal generating means to develop a function control signal;

sensing means displaced from and electrically isolated from said light source for generating an activating signal upon receipt of said function control signal;

means connected to said sensing means for assuming at least first and second states, said means for assuming being responsive to a receipt of said activating signal to assume a selected one of said at least first and second states and retain such state until a subsequently generated activating signal is received; and means responsive to said selected one of said at least first and second states for applying energizing potential to said light source.

20. The control means of claim 19 wherein said control unit comprises a dental handpiece; and said switch means is mounted upon said dental handpiece.

21. The control means of claim 20 wherein a portion of said fiber optics bundle extends through said dental handpiece so that said distal end is positioned to emit light derived from said lamp outwardly and away from the dental handpiece to illuminate the region where the dental handpiece is being used.

22. The control means of claim 20 wherein said dental handpiece is coupled to a bundle of a plurality of conduits;

one of said conduits comprising conductor means for connecting said switch means to said signal generating means.

23. The control means of claim 19 wherein said signal generating means comprises a light emitting element and said sensing means comprises a photosensitive element.

24. The control means of claim 23 wherein said light emitting element is a light emitting diode.

25. The control means of claim 23 wherein said photosensitive element is a phototransistor.

26. The control means of claim 19 wherein said signal generating means comprises a transducer adapted to vibrate responsive to operation of said switch means; and said sensing means comprising means responsive to vibration of said transducer means for generating said activating signal.

27. The control means of claim 19 wherein said means for assuming at least first and second states comprises:

counting means having a plurality of stable states including said at least first and second states, said counting means being advanced to a succeeding one of said plurality of stable states in response to each activating signal generated by said signal means, said means responsive acting to apply energizing potential to said light source when said counting means is in at least one of said plurality of stable states and to deenergize said light source when said counting means is in another of said plurality of stable states.

28. The control means of claim 19 wherein said means for assuming at least first and second states comprises:

counter means having a plurality of stable states including said at least first and second states, said counting means being advanced to a succeeding one of said plurality of stable states in response to each activating signal generated by said sensing means; and said means responsive acting to apply energizing potential at a first intensity to said light source when said counter means is in at least one of said plurality of stable states, to deenergize said light source when said counter means is in another of said plurality of stable states and to apply energizing potential at a second intensity to said light source when said counter means is in yet another of said plurality of stable states.

29. The control means of claim 19 wherein said signal generating means comprises field producing means for generating a magnetic field responsive to operation of said manually operable switch means; and
said sensing means includes second switch means responsive to said magnetic field for producing said activating signal.

30. The control means of claim 29 wherein said field producing means and said second switch means collectively comprise a reed switch assembly, said second switch means comprising cooperating reed switch elements encapsulated within an enclosure and said field generating means comprising a winding wound about said enclosure.

31. The control means of claim 19 wherein said means for
assuming at least first and second states includes counter means having a plurality of stable states, said counter means being responsive to each activating signal received to advance the state of the counter means from one stable state to the next; and wherein said means responsive comprises:
a triac and an AC signal source coupled in series with said lamp, said triac having a gate electrode and said AC signal source generating an AC signal having recurring half-cycles of a selected periodicity;
means for selectively generating a gate signal to be applied to said gate electrode, said means for generating being responsive to the state of said counter means for selectively applying said gate signal to said gate electrode under conditions where no gate signal is applied to said gate electrode when said counter means is in a first one of said stable states, a gate signal is applied to said gate electrode when said counter means is in a second one of said stable states timed to enable said triac during a first portion of each half-cycle of said AC signal, and a gate signal is applied to said gate electrode when said counter means is in a third one of said stable states timed to enable said triac during a second portion of each half-cycle of said AC signal.

32. The control means of claim 19 wherein said means for assuming includes counter means for counting the number of operations of said switch means, and said means responsive comprises:
a triac connected in series intermediate an AC signal source and said light source, said triac having a gate electrode for controlling conduction therethrough;
means for detecting the zero crossings of an AC signal provided by said AC signal source;
ramp signal generating means responsive to each zero crossing for generating a ramp signal;
decoder means coupled to said counter means for developing a signal level representative of the count in said counter;
comparator means coupled to said decoder means and said ramp signal generating means for generating a signal when the level of said ramp signal reaches the level of the signal developed by said decoder means; and means for selectively generating a gating signal in response to the output signal of said comparator means and for applying said gating signal to said gate electrode of said triac, said gating signal being applied to enable said triac to conduct at a point in each half-cycle of the AC signal which corresponds to the count in said counter means.

33. The apparatus of claim 19 wherein said signal generating means comprises a pulse generating circuit, a small DC battery source and a circuit element for producing said function control signal connected in series with said switch means;
said pulse generating circuit comprising a capacitor, whereby said circuit element is energized by a signal pulse upon momentary closure of said switch means.

34. Control means for selectively energizing a lamp serving as the illumination source for an elongated fiber optics bundle having a first end positioned adjacent to said lamp and a second end mounted at the working end of a dental handpiece, said control means comprising:
switch means;
signal generating means for generating an enabling signal in response to an operation of said switch means;
means for selectively applying AC power to said lamp; and
sensing means responsive to the enabling signal generated by said signal means for causing said means for selectively applying to couple AC power to said lamp, said signal generating means being electrically isolated from both said means for selectively applying AC power and said sensing means to protect the user of said dental handpiece, said sensing means including means for latching said means for selectively applying AC power to said lamp in a coupling relationship with said lamp until a subsequent activation of said switch means for disabling said means for selectively coupling.

35. The control means of claim 34 wherein said dental handpiece includes an air conduit for delivering air under pressure to said dental handpiece;
a branch conduit communicating with said air conduit; and
wherein said switch means comprises pressure sensitive means arranged in said branch conduit and responsive to the delivery of air under pressure to said dental handpiece through said air conduit for operating said switch means.

36. The control means of claim 35 wherein said pressure sensitive means comprises a pressure sensitive transducer for generating a signal for operating said signal generating means.

37. The control means of claim 35 wherein said pressure sensitive means comprises a normally-open pressure sensitive switch which is closed when air under pressure is introduced into said air conduit.

38. The control means of claim 35 wherein said branch conduit comprises an exhaust conduit communicating with said air conduit.

39. The control means of claim 34 wherein said switch means takes the form of manually operable switch means and said signal generating means comprises:
oscillator means coupling said oscillator means to said sensing means;

means inductively coupling said switch means to said impedance means for reducing said impedance when said switch means is operable.

40. The control means of claim 39 wherein said oscillator means comprises a high frequency oscillator.

41. The control means of claim 40 wherein said impedance means comprises an inductance.

42. The control means of claim 40 further comprising a transformer and wherein said impedance means comprises a first winding of a transformer; and said inductive coupling means comprises a second winding of said transformer which is inductively coupled to said first winding.

43. The control means of claim 42 wherein said switch means is coupled across said second winding.

44. The control means of claim 42 wherein said transformer means further comprises an iron core transformer, said first and second winding, being wound upon said iron core.

* * * * *

UNITED STATES PATENT AND TRADEMARK OFFICE
CERTIFICATE OF CORRECTION

PATENT NO. : 4,208,579

DATED : June 17, 1980

INVENTOR(S) : Leonard Scrivo, et al.

It is certified that error appears in the above-identified patent and that said Letters Patent are hereby corrected as shown below:

Column 6, line 47, the word "acceptable" should read
-- accomplished --.

Column 13, line 62, the word "dioe" should read -- diode --.

Column 14, line 4, "R2" should read -- R4 --.

Column 14, line 31, "CD 4027 Ad" should read -- CD 4027 AD --.

Column 16, line 35, the word "one" should read -- on --.

Column 17, line 38, the word "powdered" should read -- powered --.

Column 18, line 60, the word "discharged" should read
-- discharges --.

Claim 1, Column 19, line 20, the word "ans" should read
-- and --.

Claim 15, Column 21, line 10, the word "locatted" should read
-- located --.

Signed and Sealed this

Nineteenth Day of August 1980

[SEAL]

Attest:

SIDNEY A. DIAMOND

Attesting Officer

Commissioner of Patents and Trademarks